US012629192B2

(12) United States Patent
Heuer

(10) Patent No.: US 12,629,192 B2
(45) Date of Patent: May 19, 2026

(54) BONE ANCHOR FOR THE OPTIMIZED CEMENT APPLICATION

(71) Applicant: MIMEO MEDICAL GmbH, Filderstadt (DE)

(72) Inventor: Frank Heuer, Filderstadt (DE)

(73) Assignee: MIMEO MEDICAL GmbH, Filderstadt (DE)

( * ) Notice: Subject to any disclaimer, the term of this patent is extended or adjusted under 35 U.S.C. 154(b) by 365 days.

(21) Appl. No.: 18/028,733

(22) PCT Filed: Sep. 28, 2021

(86) PCT No.: PCT/EP2021/076699
§ 371 (c)(1),
(2) Date: Mar. 27, 2023

(87) PCT Pub. No.: WO2022/064071
PCT Pub. Date: Mar. 31, 2022

(65) Prior Publication Data
US 2023/0329764 A1 Oct. 19, 2023

(30) Foreign Application Priority Data
Sep. 28, 2020 (DE) ..................... 10 2020 005 927.9

(51) Int. Cl.
*A61B 17/86* (2006.01)
(52) U.S. Cl.
CPC .................................. *A61B 17/864* (2013.01)
(58) Field of Classification Search
CPC ........................... A61B 17/864; A61B 17/8811
See application file for complete search history.

(56) References Cited

U.S. PATENT DOCUMENTS

2011/0060373 A1 3/2011 Russell et al.
2019/0167326 A1* 6/2019 Greenhalgh ....... A61B 17/8605

FOREIGN PATENT DOCUMENTS

| DE | 35 08 759 | 10/1985 |
|---|---|---|
| DE | 10 2011 112 890 | 7/2012 |
| DE | 10 2011 017 602 | 10/2012 |
| EP | 2 140 824 | 6/2016 |
| EP | 3 210 554 | 8/2017 |
| WO | 2020/008309 | 1/2020 |
| WO | 2021/245169 | 12/2021 |

OTHER PUBLICATIONS

International Search Report with English Translation for PCT/EP2021/076699, mailed Jan. 28, 2022, 7 pages.
Written Opinion of the ISA for PCT/EP2021/076699, mailed Jan. 28, 2022, 8 pages.

* cited by examiner

*Primary Examiner* — Olivia C Chang
(74) *Attorney, Agent, or Firm* — Nixon & Vanderhye, PC

(57) ABSTRACT
A bone anchor for the fixation of bone components and bone fragments is disclosed including a shaft, a neck area and a head located in proximal direction, and a tip located in distal direction, the bone anchor having a substantially cylindrically shaped hollow chamber extending along the central axis, the hollow chamber being adjacent to a transition area located distally from a central plane. The transition area is located distally from the central plane, that the transition area has at least in sections an inner diameter and the hollow chamber has at least in sections an opening diameter, and the opening diameter of the hollow chamber is larger than the inner diameter of the distal transition area.

19 Claims, 8 Drawing Sheets

BONE ANCHOR FOR THE OPTIMIZED CEMENT APPLICATION

CROSS REFERENCE TO RELATED APPLICATIONS

The present application is a National Phase of International Application Number PCT/EP2021/076699 filed Sep. 28, 2021, which designated the U.S. and claims priority benefits from German Patent Application Number DE 10 2020 005 927.9 filed Sep. 28, 2020, the entire contents of each of which are hereby incorporated by reference.

STATE OF THE ART

Osteoporosis is characterized by a decrease in the structural integrity of the bone. Often, this results in compression fractures that require surgical treatment. Due to the reduced bone quality, the clinical challenge is insufficient anchorage stability when applying bone anchors.

DE3508759A1 discloses a bone screw for the treatment of femoral fractures. The patent application describes a bone screw with a centrally arranged cannulation opening and several laterally running openings, which serve to allow bone cement to be injected through the bone screw into the bone. After hardening of the bone cement, a significantly higher strength between bone and bone screw is achieved.

To enable the minimally invasive use of bone anchors, the cannulation opening must pass completely through the bone anchor so that the bone anchor can be inserted into the bone guided by a guide wire. If cementable bone anchors with a through-hole are used, however, there is a risk that bone cement can spread outside the bone during bicortical screw fixation, which can cause serious complications.

EP2140824A1 discloses bone anchors which are optimized for the provision of bone cement in such a way that they can be closed distally with a plug after minimally invasive insertion into the bone so that cement leakage is prevented. However, the disadvantage is that such a mini-plug must be kept in stock as an extra component and the handling must provide sufficient safety against accidental loss of the mini-plug. A one-piece design without moving parts would therefore be desirable.

REPRESENTATION OF THE INVENTION

The problem is solved by the bone anchor (10) according to the invention, whereby bone anchors (10) are built up together to form a unit or osteosynthesis construct (1) of two or more bone anchors. Relevant prior art is available for this, which is why it will not be discussed in detail here.

For the bone anchor (10) according to the invention, space-allocating coordinate references are defined, such as the proximal direction (101), the distal direction (102), which extend along a central axis (103). The radial propagation (104) is defined extending outward from the central axis (103). The circumferential spread (105) is defined by a constant radius and along a variable circumferential angle (FIG. 1). Furthermore, there is a central plane (106) which separates the distal (102) and proximal (10) spatial directions equally.

In a first embodiment, a bone anchor (10) for the fixation of bone components and bone fragments is described, which consists of a shaft (13), a neck area (12) and a head (11) located in proximal direction (10), as well as a tip (14) located in distal direction (102).

In addition, it is to be mentioned that the bone anchor (10) is optimally designed as a one-piece component and is manufactured with the aid of an additive process. If the bone anchor (10) cannot be manufactured using an additive process, a multi-part construction of the bone anchor is suitable, which is assembled using any method known in the prior art. The head (11) is preferably formed as a lens, inclined head or spherical head. However, a composition of different curves and surface is also conceivable. The main feature of the head is that the head (11) has a larger outer diameter than the neck area (12). Preferably, the bone anchor has a tool attachment point (19) suitable for introducing a torque. For minimally invasive treatment, it is advantageous if the bone anchor has a cannulation opening (15, 16, 40, 20) passing completely through it, which can be used to guide a surgical guide wire.

Bone screws that can be screwed to a bone are preferably used as bone anchors. However, hooks, clamps, nails and other types of bone anchors can also be used. In the example of a bone anchor (10) provided here, a bone screw with a shaft (13) and a bone thread (131) located on the shaft is presented. The thread (131) may have a finer toothing (132) in sections, which is more suitable for a harder cortical bone. A tapered thread (132) with a cutting edge (133) at the bone anchor tip (14) is advantageous so that the bone anchor can self-tap into the bone when screwed in.

In the case of weak bone, such as osteopenia or osteoporosis, it may be necessary to additionally augment the bone anchor. This can be done with bone cement. Bone cement is preferably a polymer consisting of at least two components mixed together and injected in a liquid or paste-like state. After a few minutes, the bone cement hardens in the bone to form a plastic and bonds with the sponge-like bone structure. A polymethyl methacrylate cement is usually applied. Alternatively, other media for delivery through the bone anchor are possible. Alternative media, such as pharmaceutically active media, or media containing cells, nutrients, or media serving as hereditary information carriers, or vaccines can possibly be administered through the bone anchor. Therefore, throughout this document, the injectable medium is referred to simply as liquid (17).

Inside the bone anchor (10) is a mainly cylindrically shaped hollow chamber (40) extending along the central axis (103) (FIG. 2), the hollow chamber (40) being adjacent to a transition area (20) located distally (102) from a central plane (106). This transition area (20) has an inner diameter (d20) at least in sections, and the hollow chamber (40) has an opening diameter (d40) at least in sections. The opening diameter of the hollow chamber (d40) is larger than the inner diameter (d20) of the distal transition area (20). This difference in cross-section (cf. d40 and d20) makes it more difficult for the liquid (17) to flow back when it is already in the hollow chamber (40).

The hollow chamber (40) is provided in distal-proximal alignment mainly centrally inside the bone anchor (10). As described above, it is advantageous that the hollow chamber (40) is configured such that it extends at least in sections with a constant opening diameter (d40) along the central axis (103) and that the hollow chamber (40) is adjacent to at least one transition area (20). Optionally, the hollow chamber (40) has at least one laterally extending opening (411, 412, 421, 422) interacting with the hollow chamber. Preferably, the openings are arranged in peripheral direction in ring-like formation (41 or 42). In the case of more than one peripheral direction ring-like opening formation (41 and 42), the openings have different opening diameters for each formation. In the case of bone anchors (10) screwed into a bone, the lateral openings interact with the surrounding bone tissue from the hollow chamber (40). They are configured to ensure that the liquid (17) injected into the bone anchor (10) is delivered through the lateral openings into the surrounding tissue. A different diameter of the opening formations (41, 42) is advantageous in that, due to the local pressure difference within the liquid (17), a similar volume flow is generated through all openings (411, 412, 421, 422). This is made possible by the fact that the openings (411, 412, 41) that are closer to the distal transition area (20) have a larger diameter than the openings (421, 422) of the formation (42) that are further proximal.

In the further proximal course (101) along the central axis (103), i.e. after the main chamber (40), there is an opening (16) which is suitable for receiving a cannula at least in sections (FIG. 2). The opening diameter (d16) of the opening (16) adjacent to the proximal main chamber (40) is optionally larger than at least a portion of the inner diameter (d40) of the proximal main chamber (40). Furthermore, it is preferable if the opening (16) opens in the proximal direction (101) into the tool attachment point (19).

This difference in diameter (d20, d40) results in the liquid (17) preferably being discharged through the aforementioned lateral openings (411, 412, 421, 422) to the surrounding tissue without being able to escape distally (102) through a distal opening (15).

Preferably, the distal opening (15) has a smaller diameter (d15) than the inner diameter of the hollow chamber (d40), whereby it is advantageous that the diameter of the distal opening (d15) is approximately equal to the inner diameter of the distal transition area (20), which is present at least in sections. This means that an inserted guide wire does not undergo any further diameter changes at the distal opening (15).

As already mentioned, the hollow chamber (40) is directly adjacent to at least one transition area (20). At least some sections of the transition area have a smaller opening diameter (d20) than the hollow chamber (d40). The reduced opening diameter (d20) increases the dynamic pressure of a liquid (17) forced through the transition area (20). This results in an obstacle for the liquid (17), which would be equivalent to a partially permeable barrier. This can be measured, for example, via the flow resistance. The flow resistance can be influenced by a pressure difference in the liquid (17), the internal friction, the viscosity and the volume flow of the liquid (17). Structurally, the flow resistance can be influenced by the surface friction, a surface roughness, the diameter and the length of the section to be overcome.

The object of a transition area (20) according to the invention is, as soon as the liquid (17) is in the hollow chamber (40), to ensure that the liquid (17) flows off preferably through the lateral openings (41, 42) and that the risk of unintentional passage of the liquid (17) through the transition areas (20) is minimized. Therefore, the object of the transition area (20) is to provide a section which generates a high flow resistance within the transition area (20) in sections compared to the hollow chamber (40). Preferably, the effect of the flow resistance should be direction-dependent (21, 22) on the flow direction of the liquid (17).

In a preferred embodiment, at least the transition area (20) applies a flow resistance, or generates a pressure difference, or affects the internal friction of the liquid (17), or generates a higher surface friction, or affects the volume flow; the difference(s) being higher in a blocking direction (22) than in a forward direction (21). This structure results in a type of fluidic diode, which is shown with a diode symbol in the following figures (FIG. 3a). It is thus possible to distinguish between a forward direction (21) and a blocking direction (22). However, it is important to mention that in blocking direction (22) the fluid flow cannot be stopped 100%, because there is always an opening (d20) centrally in the transition area (20). Rather, with a transition area, the risk of unintentional leakage can be reduced or not completely prevented.

In FIG. 3a, it can be seen that the hollow chamber (40) is distally adjacent to a transition area (20) as viewed from a central plane (106) and the distal transition area (20) has a forward direction (21) in proximal direction (101). It can also be seen that the hollow chamber (40) is distally adjacent to a transition area (20) when viewed from a central plane (106) and the distal transition area (20) has a blocking direction (22) in distal direction (101).

The functionality of the fluidic diode (20) is shown in FIGS. 3b, 4 and 4b. FIG. 3b displays a simplified model structure of the bone anchor. The hollow chamber (40) is shown as a container adjacent to the fluidic diode (20). An inlet is provided (16), through which a cannula can inject a liquid (17). The hollow chamber (40) has at least one outlet, which is simplified by the lateral openings (41, 42, 411, 412, 421, 422). For completeness, the distal opening (15) is schematically displayed as a drain. From the schematic FIG. 4, it can be seen how the fluid flow is formed as soon as a liquid (17) is injected through the feed line (16). The distal fluidic diode (20) is arranged in blocking direction and prevents the liquid from leaking to distal direction (102). The liquid can escape through the lateral openings (41, 42 etc.). The distal transition area (20) prevents cement leakage to the distal direction (102) so that no bone cement can leak into the surrounding tissue.

The simplest fluidic diode structure can be obtained using radially inwardly directed area elements (24). The transition area (20) consists of at least one segment (29) having at least one area element (25, 272, 273) defining the inner opening diameter (d20) and at least one area element (26) defining a dam space, and at least one area element (24) generating a dynamic pressure in blocking direction (22), wherein the area element (24) is arranged at an angle to a vertical of the central axis (103) between −20° and 20°. The blocking area elements (24) cause a resistance, which leads to a local increase of the dynamic pressure and thus causes a back-pressure in the liquid (17) and makes it more difficult for the liquid to pass through the transition area (20). The blocking area elements can be planar (FIG. 5a, b), or concave (FIG. 6a, b), or convexly curved, or have polygonal elements. It is advantageous if such an arrangement of area elements and their configurations are replicated segment by segment (29) along the central axis (103). This creates an amplification effect of the blocking direction (22). For completeness, it is also necessary to mention area elements (23) that promote a forward direction (21) of a liquid (17). They do not provide an increased dynamic pressure compared to the blocking direction (22). The area elements (e.g. 23, 24, 25, 26) are preferably provided as rotary discharges rotating around the central axis (103) in peripheral direction (105). Alternatively, the area elements can also be discharged in a helix along the central axis (103). This means that the area elements can also be produced in a conventional rotary or milling process.

According to an alternative embodiment, the fluidic diode (20) is provided to cause a dynamic influence on the flow of the liquid (17) and is thus more effective. Optimally, the blocking area elements (24) have at least a concave curvature (FIG. 7a, b and FIG. 8). To prevent the liquid from accumulating and remaining there, it is advantageous if a continuous flow of liquid is generated, which permanently increases the dynamic pressure and counteracts or changes the main flow of liquid. This can be achieved by the transition area (20) consisting of at least one segment (29) having at least one area element (26) defining a dam space, and in said dam space having a ring (27) disposed therein. The ring (27) is located within a concentric discharge (26) and is supported by support elements (273) interacting with the outer wall (13) of the bone anchor (11). Between the support elements, outer wall and ring are intermediate spaces which serve to divert the fluid flow.

The inner side (272) of the ring (27) defines the opening diameter of the transition area (d20). Optimally, the ring (27) is convexly curved on its radial outer side (271). The convex curvature provides a Coanda effect in the liquid, so that the liquid is not dammed up but diverted into the main flow.

BRIEF DESCRIPTION OF THE DRAWINGS SHOW

FIG. 1 an oblique view of the bone anchor according to the invention,

FIG. 2 a side view and associated sectional view through the bone anchor according to the invention, FIG. 3a a further sectional view, showing a simplified representation of a fluidic diode, FIG. 3b a model-like representation of the components relevant to fluid flow, FIG. 4 illustrates in use during application of a liquid through a cannula.

Figure 1:
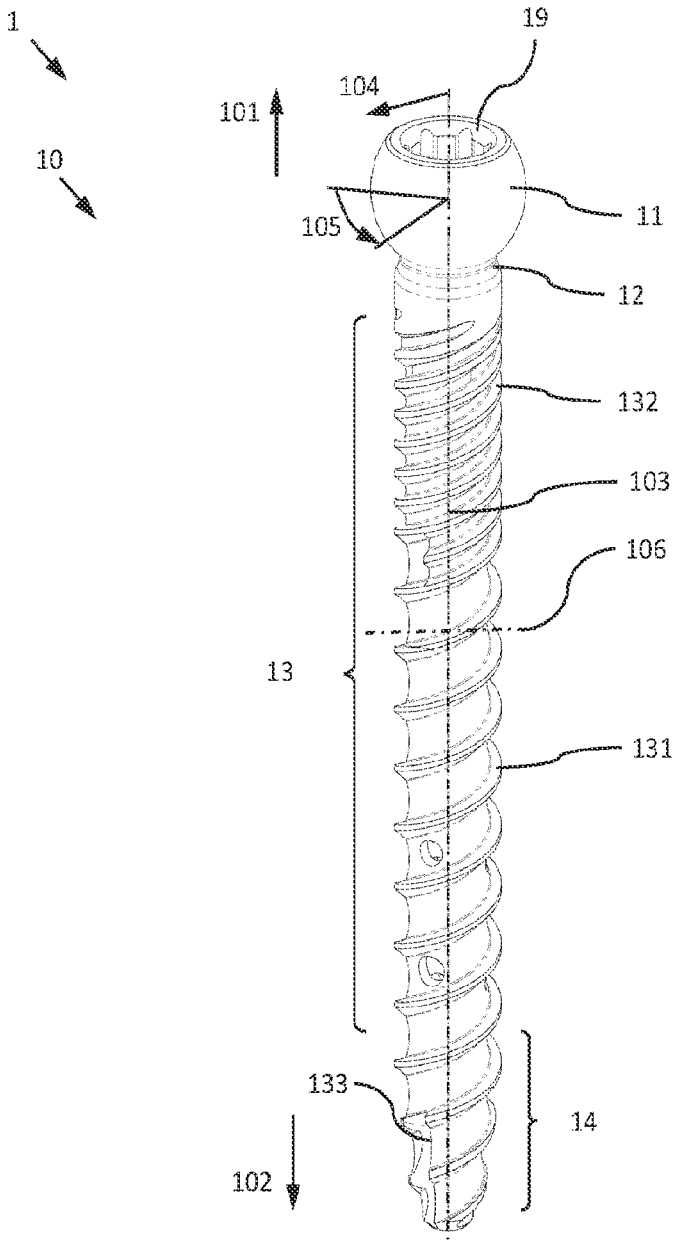
Figure 2:
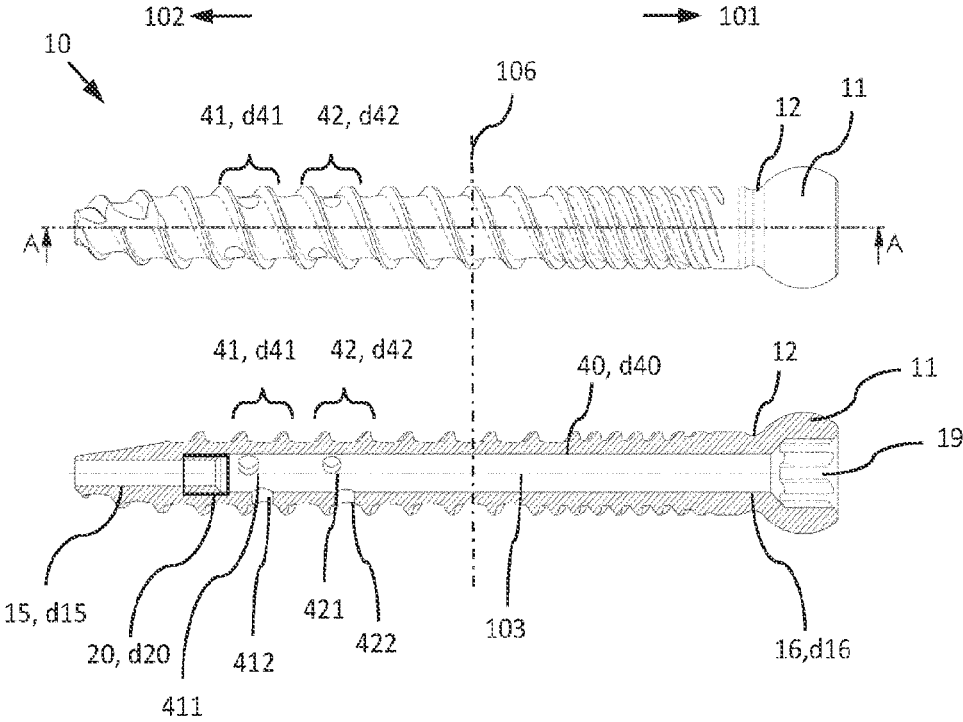
Figure 3A:
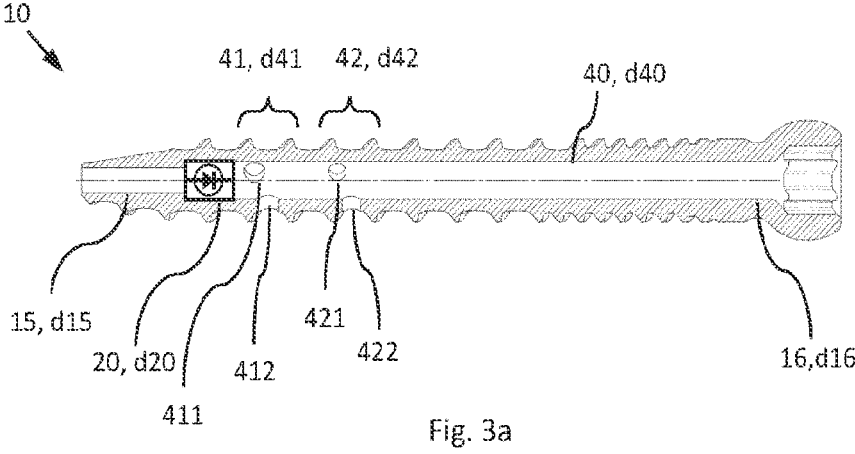
Figure 3B:
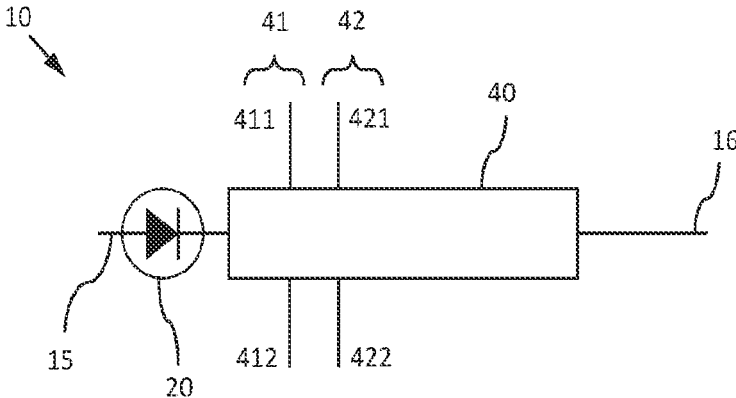
Figure 4:
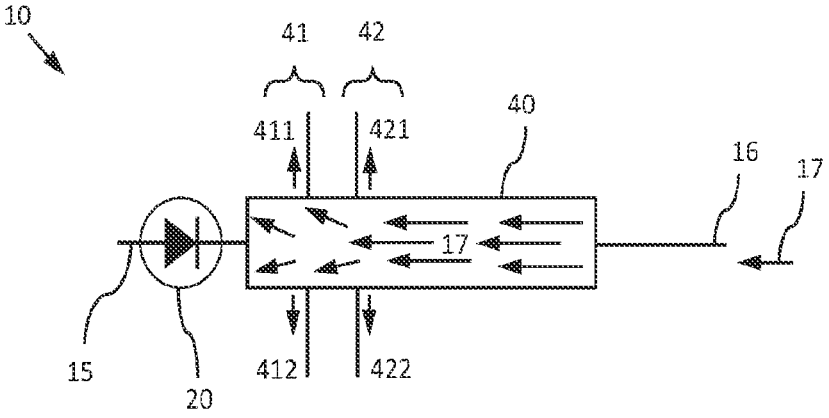
Figures 5A, 5B:
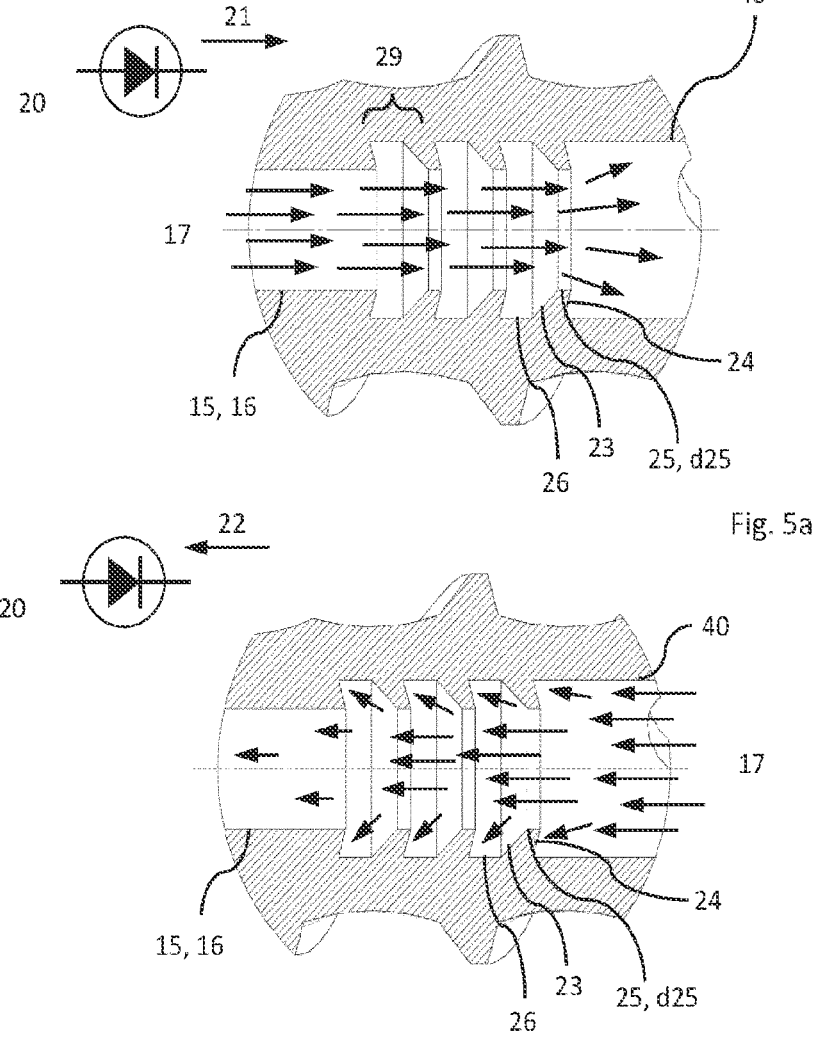
FIG. 5a shows a structure of a simple fluidic diode in forward direction.
FIG. 5b shows a structure of a simple fluidic diode in blocking direction.
Figures 6A, 6B:
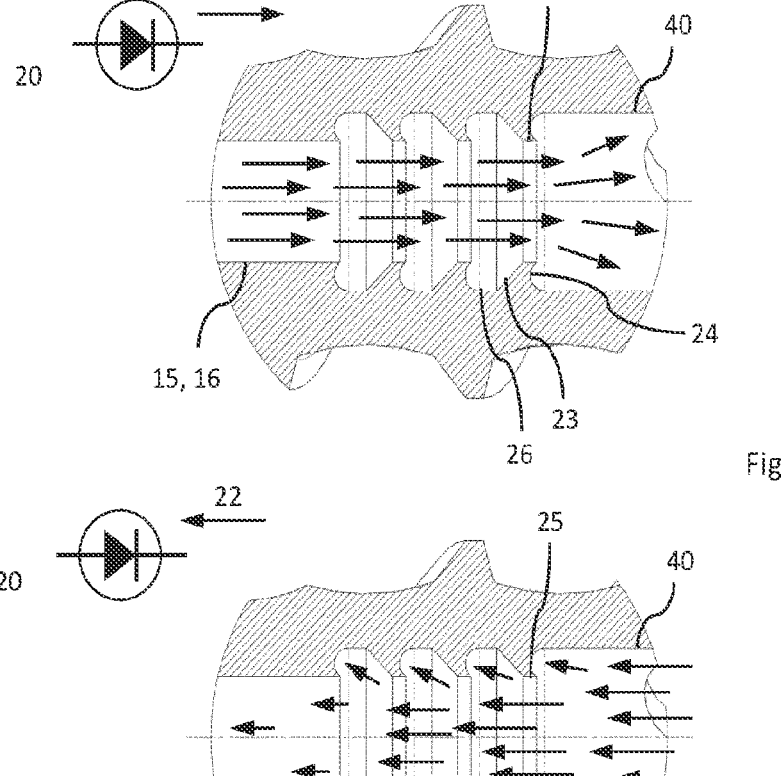

FIG. 6a the structure of an alternative form of fluidic diode in forward direction.

FIG. 6b shows the structure with fluidic diode in blocking direction.

Figures 7A, 7B:
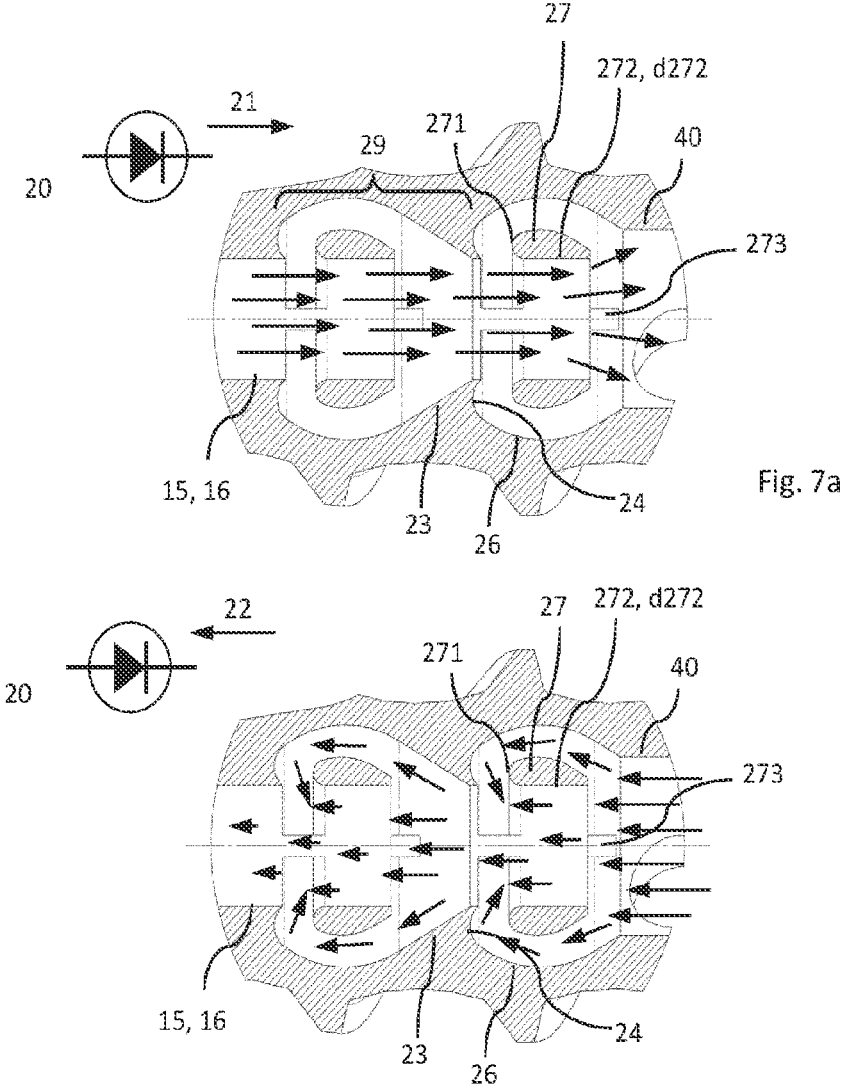

FIG. 7a an alternative embodiment of a fluidic diode in the forward direction.

FIG. 7b displays a fluidic diode in the reverse flow principle.

Figure 8:
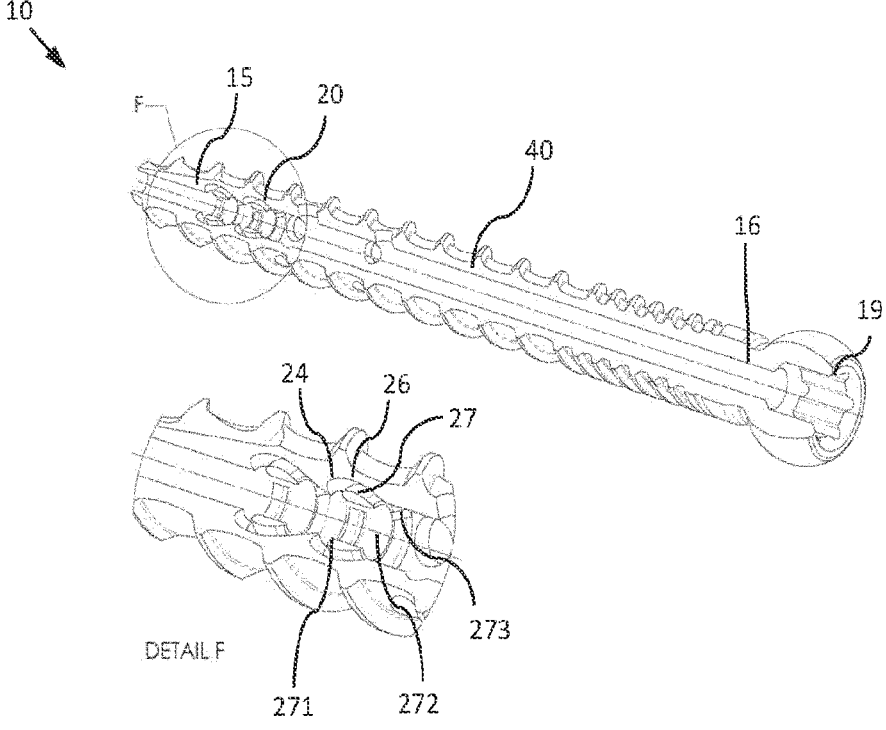

FIG. 8 a ¾ section in an oblique view from FIG. 7a/b.

The invention claimed is:

1. A bone anchor for the fixation of bone components and bone fragments, comprising:
a shaft, a neck area and a head located in proximal direction, and a tip located in distal direction, the bone anchor having a substantially cylindrically shaped hollow chamber extending along the central axis,
wherein the hollow chamber is adjacent to a transition area located distally from a central plane,
wherein the transition area is located distally from the central plane, that the transition area has at least in sections an inner diameter and the hollow chamber has at least in sections an opening diameter, and the opening diameter of the hollow chamber is larger than the inner diameter of the distal transition area, and the transition area causes at least one difference in the flow resistance, or pressure difference, or internal friction of the liquid, or volume flow, and this difference is dependent on a flow direction of a liquid,
wherein the transition area further comprises at least one segment having at least one area element defining the inner opening diameter and at least one area element defining a dam space, and at least one area element generating a dynamic pressure in blocking direction, wherein the area element is arranged at an angle to a vertical of the central axis between −30° and 30°, said area element being planar, concave or convex curved.

2. The bone anchor according to claim 1, wherein at a proximal region along the central axis an opening adjoins the proximal region of the hollow chamber, which is suitable for receiving a cannula at least in sections.

3. The bone anchor according to claim 2, wherein the opening diameter of the opening adjacent to the proximal region of the hollow chamber is at least equal to or greater than at least a portion of the inner diameter of the hollow chamber.

4. The bone anchor according to claim 2, wherein the opening opens in a proximal direction in a tool attachment point.

5. The bone anchor according to claim 1, wherein the transition area defines a section which causes a higher flow resistance compared to a section of the same length of the hollow chamber.

6. The bone anchor according to claim 1, wherein the transition area defines a section that causes a higher pressure difference in the liquid compared to a section of the same length in the hollow chamber.

7. The bone anchor according to claim 1, wherein the transition area defines a section that results in a higher internal friction in the liquid compared to a section of the same length of the hollow chamber.

8. The bone anchor according to claim 1, wherein the transition area has a higher surface friction coefficient or a higher surface roughness than the hollow chamber.

9. The bone anchor according to claim 1, wherein the transition area allows a smaller volume flow of liquid than the hollow chamber.

10. The bone anchor according to claim 1, wherein the transition area further comprises at least one segment having at least one area element defining a dam space, and a ring or at least one ring segment is arranged at least partially in said dam space.

11. The bone anchor according to claim 10, wherein the ring defines the opening diameter of the transition area with its inner side.

12. The bone anchor according to claim 10, wherein the ring is convexly curved at its radial outer side.

13. The bone anchor according to claim 1, wherein the transition area has a blocking direction and a forward direction for fluids.

14. The bone anchor according to claim 1, wherein the hollow chamber is distally adjacent to a transition area as viewed from the central plane and the distal transition area has a forward direction in proximal direction.

15. The bone anchor according to claim 1, wherein the hollow chamber is distally adjacent to a transition area as viewed from the central plane and the distal transition area has a blocking direction in distal direction.

16. The bone anchor according to claim 1, wherein the hollow chamber has at least one laterally extending opening communicating with the hollow chamber, and in case of more than one opening the openings are arranged in peripheral direction in ring-like formation, and in case of more than one in peripheral direction ring-like formation, the openings and have different opening diameters for each formation.

17. The bone anchor according to claim 1, wherein the bone anchor is built in one piece.

18. The bone anchor according to claim 1, wherein the bone anchor is cannulated throughout.

19. The bone anchor according to claim 1, wherein the at least one segment is replicated along the central axis and interact with each other.

\* \* \* \* \*